US005571786A

United States Patent [19]
Eibl et al.

[11] Patent Number: 5,571,786
[45] Date of Patent: Nov. 5, 1996

[54] USE OF PROTEIN C OR THE ACTIVATION PEPTIDE OF PROTEIN C FOR PREPARING A PHARMACEUTICAL PREPARATION

[75] Inventors: Johann Eibl; Ludwig Pichler; Hans P. Schwarz; Peter Turecek, all of Vienna, Austria

[73] Assignee: Immuno Aktiengesellschaft, Vienna, Austria

[21] Appl. No.: 375,777

[22] Filed: Jan. 20, 1995

Related U.S. Application Data

[63] Continuation-in-part of Ser. No. 18,910, Feb. 17, 1993, abandoned, which is a continuation of Ser. No. 694,213, Apr. 19, 1991, abandoned.

[30] Foreign Application Priority Data

| Aug. 16, 1990 | [AT] | Austria | A1697/90 |
| Jan. 28, 1991 | [EP] | European Pat. Off. | 91890012 |

[51] Int. Cl.⁶ ............................................. A61K 38/16
[52] U.S. Cl. ............................................................. 514/8
[58] Field of Search ............................................. 514/8

[56] References Cited

U.S. PATENT DOCUMENTS

| 4,518,608 | 5/1985 | Kahan | 514/420 |
| 4,604,285 | 8/1986 | Smith et al. | 424/94.6 |
| 4,772,585 | 9/1988 | Sarnoff et al. | 514/2 |
| 4,849,403 | 7/1989 | Stocker et al. | 530/381 |
| 4,902,614 | 2/1990 | Wakabayoshi et al. | 530/381 |
| 4,908,314 | 3/1990 | Orthner | 435/219 |
| 4,944,943 | 7/1990 | Eschenfelde et al. | 424/94.64 |
| 5,009,889 | 4/1991 | Taylor et al. | 424/94.64 |
| 5,084,273 | 1/1992 | Hirahara | 424/94.6 |
| 5,084,274 | 1/1992 | Griffin et al. | 424/94.64 |
| 5,093,117 | 3/1992 | Lawrence et al. | 424/85.8 |
| 5,151,268 | 9/1992 | Bang et al. | 424/94.64 |

OTHER PUBLICATIONS

English language abstract of PCT Patent No. WO 9008556 (corresponding to U.S. Pat. No. 5,093,117).

English language abstract of European Patent No. EP 326014 (corresponding to U.S. Pat. No. 5,084,273).

P. C. Comp et al., "Evidence for multiple roles for activated protein C in fibrinolysis", Chemical Abstracts vol. 93 No. 3, 1980, p. 424.

P. C. Comp et al., "Generation of fibrinolytic activity by infusion of activated protein C into dogs", Chemical Abstracts vol. 95 No. 25, 1981, p. 347.

G. Kohler et al., "Continuous Cultures of Fused Cells Secreting Antibody of Predefined Specificity", Nature, 256:495–497, (1975).

Randall et al., "A Method For Measurement of Analgesic Activity On Inflamed Tissue", Arch. Int. Pharmacodyn., CXI, 4:409–419, (1957).

Kisiel et al., "Isolation, Characterization, and Mechanism of Activation by α–Thrombin", (1979) J. Clin. Invest. 64:761–769.

Kisiel et al., "Anticoagulant Properties of Bovine Plasma Protein C Following Activation by Thrombin", (1977) Biochemistry 16(26):5824–5831.

Taylor et al., "Protein C Prevents the Coagulopathic and Lethal Effects of *Escherichia coli* Infusion in the Baboon", (1987, Mar.) J. Clin. Invest. 79:918–925.

Suzuki et al., "Inactivation of Human Coagulation Factor V by Activated Protein C", (1983) J. Biol. Chem. 258(3):1914–1920.

Esmon et al., "Proteolytic Formation and Properties of γ–Carboxyglutamic Acid–domainless Protein C", (1983) J. Biol. Chem. 258(9):5548–5553.

Esmon et al., "Inflammation and Coagulation: Linked Processes Potentially Regulated Through a Common Pathway Mediated by Protein C", (1991, Jul. 12) Thrombosis Hemostasis 66(1):160–165.

Johnson et al., "Structural Changes Required for Activation of Protein C Are Induced by $Ca^{2+}$ Binding to a High Affinity Site That Does Not Contain γ–Carboxyglutamic Acid", (1983) J. Biol. Chem. 258(9):5554–5560.

The Merck Index (1983) Tenth Ed., p. 123.

Comp et al., "Generation of Fibrinolytic Activity by Infusion of Activated Protein C Into Dogs", (1981) J. Clin. Invest. 68:1221–1228.

Esmon et al, "Protein C and the Endothelium", Seminars in Thrombosis and Hemostasis, vol. 14 (2), 1988, pp. 210–215.

Zurborn et al., Biological Abstracts, vol. 85 (1988), No. 37736.

G. Kohler et al., "Continuous Cultures of Fused Cells Secreting Antibody of Predefined Specificity", Nature, 256:495–497, (1975).

Randall et al., "A Method For Measurement of Analgesic Activity On Inflamed Tissue", Arch. Int. Pharmacodyn., CXI, 4:409–419, (1957).

Jorens et al *Blut* 1990 61 pp. 307–310.

Roper, "New Amerc. Pocket Medical Dictionary", p. 30 ©1978.

*Primary Examiner*—John W. Rollins
*Assistant Examiner*—Deborah K. Ware
*Attorney, Agent, or Firm*—Brumbaugh, Graves, Donohue & Raymond

[57] ABSTRACT

There is disclosed the use of protein C and/or the activation peptide of protein C for preparing a pharmaceutical preparation having anti-nociceptive activity. This pharmaceutical preparation is useful in the treatment of painful conditions caused by acute or chronic inflammatory processes (such as rheumatoid arthritis, myositis, gastritis, colitis, inflammations in the urogenital tract).

4 Claims, 5 Drawing Sheets

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..12

( x i ) SEQUENCE DESCRIPTION: SEQ ID NO:1:

Asp Thr Glu Asp Gln Glu Asp Gln Val Asp Pro Arg
        1                       5                                 10

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..12

( x i ) SEQUENCE DESCRIPTION: SEQ ID NO:2:

Glu Asp Gln Val Asp Pro Arg Leu Ile Glu Gly Lys
        1                       5                                 10

( 2 ) INFORMATION FOR SEQ ID NO:3:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..31

( x i ) SEQUENCE DESCRIPTION: SEQ ID NO:3:

Tyr Gly Gly Phe Met Thr Ser Glu Lys Ser Gln Thr Pro Leu
        1                       5                                 10

Val Thr Leu Phe Lys Asn Ala Ile Ile Lys Asn Ala Tyr Lys
        15                         20                         25

Lys Gly Glu
            30

( 2 ) INFORMATION FOR SEQ ID NO:4:

```
( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..5

( x i ) SEQUENCE DESCRIPTION: SEQ ID NO:4:

Tyr   Gly   Gly   Phe   Met
        1                         5

( 2 ) INFORMATION FOR SEQ ID NO:5:

( i ) SEQUENCE CHARACTERISTICS:
            ( A ) LENGTH: 5 amino acids
            ( B ) TYPE: amino acid
            ( D ) TOPOLOGY: linear ( i i ) MOLECULE TYPE: peptide ( i x ) FEATURE:
            ( A ) NAME/KEY: Peptide
            ( B ) LOCATION: 1..5

( x i ) SEQUENCE DESCRIPTION: SEQ ID NO:5:

Tyr   Gly   Gly   Phe   Leu
            1                         5
```

USE OF PROTEIN C OR THE ACTIVATION PEPTIDE OF PROTEIN C FOR PREPARING A PHARMACEUTICAL PREPARATION

SPECIFICATION

This application is a continuation-in-part of application Ser. No. 08/018,910 filed Feb. 17, 1993, now abandoned, which is a continuation of application Ser. No. 07/694,213 filed Apr. 19, 1991, abandoned.

BACKGROUND OF THE INVENTION

The invention relates to a new use of protein C in preparing a pharmaceutical preparation. The invention also relates to new pharmaceutical preparations containing the activation peptide of protein C, optionally admixed with protein C or activated protein C.

Protein C is a vitamin K-dependent glycoprotein that is synthesized in the liver and circulates in plasma as an inactive zymogen at a concentration of about 4 µg/ml. It is converted into an active serine protease, activated protein C, by the thrombin-thrombomodulin complex on the surface of the vessel wall (endothelium). It is known that activated protein C has profibrinolytic properties. It also has an anticoagulant effect, since it proteolytically degrades both Factor Va, the cofactor for Factor Xa-induced prothrombim activation (thrombin formation), and Factor VIIIa, the cofactor for Factor IXa-induced Factor X activation.

The protein C zymogen circulates in the plasma primarily in a two-chain form containing a heavy and light chain that are disulfide bonded to one another. Activation of protein C involves the cleavage of the $NH_2$—terminal 12 amino acids of the heavy chain of the molecule. Cleavage occurs between $Arg^{12}$—$Lys^{13}$ of the heavy chain to release the activation peptide of protein C, which has the following amino acid sequence (designated as SEQ. ID. NO. 1):

$NH_2$-Asp-Thr-Glu-Asp-Gln-Glu-Asp-Gln-Val-Asp-Pro-Arg-COOH

Patients that are deficient in or lacking protein C show pronounced thrombotic or clotting tendencies. Babies born with a complete deficiency of protein C exhibit massive disseminated intravascular coagulation (DIC) and a necrotic syndrome that can lead to death in the first few weeks of life, if untreated.

Activated protein C has anticoagulant properties and has been shown to protect animals against the coagulopathic and lethal effects of endotoxin shock. Taylor, et al., *J. Clin. Invst.* 79:918–925 (1987).

Moreover, in U.S. patent application Ser. No. 540,357 a pharmaceutical preparation is described which contains protein C and may be employed for the treatment or the prevention of thromboses and thromboembolic complications.

More specifically, it is activated protein C that can inhibit arterial thrombolytic occlusion or thromboembolism. (See, e.g., U.S. Pat. No. 5,084,274 of Griffin et al.). The nonactivated zymogen does not have this effect. For example in Gruber, et al., *Blood* 73:639–642 (1989), the in vivo anti-thrombotic properties of activated human protein C were studied in a baboon model of thrombus formation on prosthetic vascular grafts. Thrombotic occlusion was prevented in animals infused with activated protein C, but was not in those (control) animals administered protein C or saline.

Recently, a $Ca^{2+}$ dependent monoclonal antibody, HPC-4, that specifically recognizes an epitope in the activation region of protein C has been described. See, e.g., U.S. Pat. No. 5,202,253 of Esmon et al. This antibody, which recognizes an epitope spanning residues 6–17 at the $NH_2$ terminus of the heavy chain of protein C, i.e., the activation region, binds to protein C, but not to activated protein C. The amino acid sequence (SEQ. ID. NO. 2) of the peptide specifically recognized by the HPC-4 antibody is:

$NH_2$-Glu-Asp-Gln-Val-Asp-pro-Arg-Leu-Ile-Glu-Gly-Lys-COOH

Administration of HPC-4 to animals in vivo has been shown to block the activation of protein C and may be useful in stemming blood loss during surgical or other procedures. See, e.g., WO 94/02172.

It has now been found that protein C, specifically the activation peptide of protein C, has anti-nociceptive and anti-inflammatory activities and may be useful in compositions and methods for alleviating or treating the pain associated with the inflammatory process.

SUMMARY OF THE INVENTION

The object of this invention is to broaden the therapeutic field of protein C, specifically the activation peptide of protein C, by using protein C and/or the activation peptide of protein C in the production of a pharmaceutical preparation that has an anti-nociceptive effect. Nociceptive may be defined as receiving injury as by a receptive neuron for painful sensations. Nociceptors are receptors which are stimulated by injury, e.g., a receptor for pain. By anti-nociceptive is meant an agent that reduces or eliminates a pain reaction resulting from an injury or tissue damage, e.g., inflammation.

The invention is based on the novel and unexpected finding that the increased sensitivity to pain induced by inflammatory processes can be reduced by protein C, and, specifically, by the activation peptide of protein C. Surprisingly, it has been found that the activation peptide of protein C, which is cleaved from the $NH_2$ terminus of the heavy chain when protein C is activated by thrombin-thrombomodulin, plays a central role in the aforementioned anti-nociceptive effects of protein C.

It has been shown that the pain threshold is significantly decreased upon administration of an antibody that is specific for the activation peptide, i.e., one that can prevent activation of protein C, and has no reactivity to activated protein C, e.g., antibody HPC-4. Thus, it has been shown that the activation peptide of protein C is specifically involved in mediating the novel anti-nociceptive and anti-inflammatory effects of protein C.

The anti-nociceptive effect in animals and analgetic effect in humans of endogenous peptides of the β-endorphine type and sequences derived therefrom (Met-enkephalin and Leu-enkephalin) are well known.

The unexpected anti-nociceptive effect of the activation peptide of protein C may be enhanced by administration in admixture with peptides of the endogenous β-endorphine type. Alternatively fusion peptides comprising the sequence of both the activation peptide of protein C and a peptide of the endogenous β-endorphine type may be administered in order to provide an enhanced anti-nociceptive effect. Preferably the individual peptides and/or fusion peptides are prepared preferably via chemical synthetic techniques known in the peptide synthesis arts.

The peptides may be understood to contain exactly the amino acid sequence described or analogues and derivates thereof, as long as their efficacy is proven in an animal model of hyperalgesia.

Due to proteolytic degradation in the circulation, peptides administered intravenously often have a relatively short biological half-life. The half-life may be improved by entrapping the peptides into liposomes for administration. An additional effect of administering the peptides in liposomal microcapsules provides a significantly increased affinity to neuronal receptors and passage through the blood brain barrier into the brain (and its pain receptors). This is a direct result of the entrapment of generally hydrophilic peptides in a lipophilic carrier (liposome). Both effects—the reduced proteolytic degradation and the increased lipophilicity—prolong and further enhance the anti-nociceptive effect of the peptides, the peptide mixtures and fused peptides.

The ratio of peptide to lipid in such a liposome preparation is in the range of about 1:100 to 1:1 (w/w), with the preferred ratio being in the range of about 1:100 to 1:5 (w/w).

The microencapsulation of the peptides and/or of protein C and/or of activated protein C also enables the formulation of a preparation which may also be administered by the oral route.

The invention also includes the use of protein C and/or the activation peptide of protein C in preparing a composition for the treatment of pain caused by acute or chronic inflammatory processes. Such pain may be the consequence of such inflammatory processes resulting from posttraumatic or postoperative conditions or caused by primary or secondary malignant diseases.

Protein C and/or the activation peptide of protein C may be used, in particular, to obtain a preparation for use in treating pain induced by rheumatoid arthritis, myositis, gastritis, colitis or inflammations of the urogenital tract, or which is associated with acute or chronic graft rejections.

Furthermore, protein C and/or the activation peptide of protein C may be capable of preventing the adhesion of leukocytes to the vessel walls and inhibiting the migration of leukocytes through permeabilized vessel walls. Both protein C and the activation peptide of protein C appear to attenuate the activation of the leukocytes and prevent complement activation.

For this reason, the invention also relates to the use of protein C and/or the activation peptide of protein C in the production of a pharmaceutical composition for the treatment of acute or chronic inflammatory diseases. Such inflammatory diseases may occur posttraumatically, postoperatively, or in the course of primary or secondary malignant diseases.

A pharmaceutical preparation containing a therapeutically effective amount of protein C and/or the activation peptide of protein C is particularly suitable for the treatment of inflammatory diseases such as rheumatoid arthritis, myositis, gastritis or colitis, for the treatment of inflammations of the urogenital tract, as well as for the treatment of inflammatory processes associated with acute or chronic graft rejections.

The pharmaceutical preparation according to the invention preferably contains protein C and/or the activation peptide of protein C, which may be purified from a biological source, such as plasma or a plasma fraction or from a culture medium of cells that naturally produce protein C or produce it as a result of recombinant DNA techniques. Such preparations are treated to inactivate any virus which is potentially present in the biological source. Heat treatment is preferred as a means of virus inactivation, e.g., by use of the method according to EP-B-O 159 311 or EP-A-O 519 901, which describes a combination of heat treatment and treatment with a tenside to inactivate any viruses.

The activation peptide of protein C for use in the present invention may be obtained by cleavage of protein C purified from a biological source, as above, or chemically synthesized. Activation of protein C can be accomplished in vitro using an activator, e..g., immobilized thrombin. The activation peptide of protein C may be separated from the mixture of activated protein C and the activation peptide of protein C resulting from activation and formulated into a pharmaceutically acceptable preparation or formulated as a mixture of the activated protein C and the activation peptide.

The invention also contemplates the use of protein C and/or the activation peptide of protein C for the production of a combined pharmaceutical preparation, including at least one antiphlogistic and/or at least one analgesic. Alternatively, protein C and/or the activation peptide of protein C can be used in preparing a pharmaceutical composition that also contains a $\beta$-endorphin-type peptide, e.g., Met-enkephalin or Leu-enkephalin. It has been shown that such combined pharmaceutical preparations exhibit synergistic effects; i.e., an increased anti-nociceptive effect.

The invention further relates to the use of protein C and/or the activation peptide of protein C in obtaining preparations for normalizing increased vascular permeability, for preventing defects of permeability of the vessel wall and for stimulating $\beta$-adrenoceptors.

DETAILED DESCRIPTION OF THE INVENTION

Figure 1:
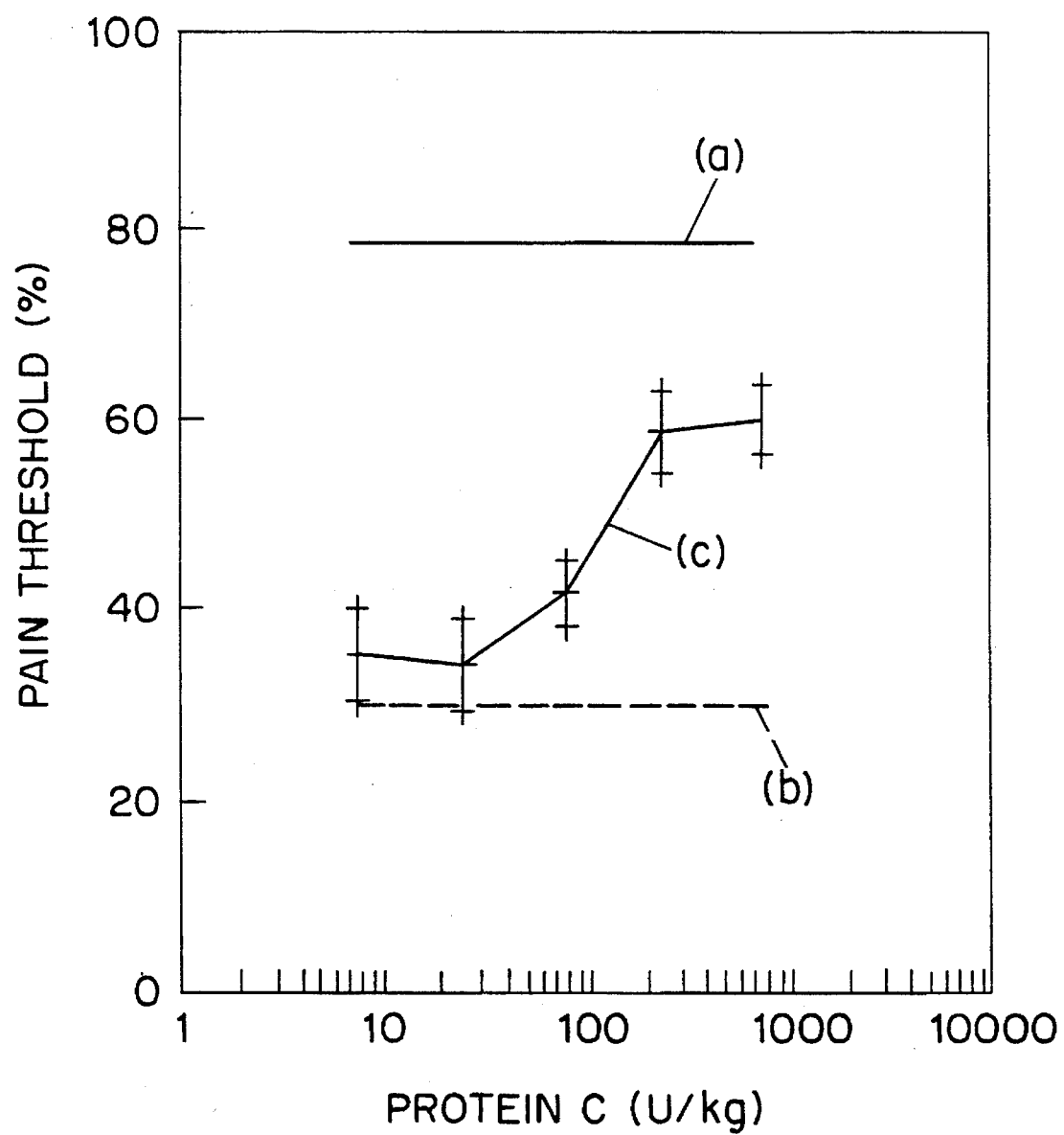
FIG. 1 is a graph depicting pain threshold in the rat paw model measured without administration of carrageenan (line a); following administration of carrageenan (line b); following administration of carrageenan and different doses of protein C (line c).

The preparation of protein C and of the activation peptide of protein C, as well as the assessment of their anti-nociceptive and other activities are described in the following section. Also described is the assessment of HPC-4, as a representative $Ca^{2+}$ dependent antibody having specificity towards the activation region of protein C, as an antagonist of the anti-nociceptive and other activities of protein C and/or the activation peptide of protein C.

EXAMPLE 1

Preparation of Protein C

Highly purified protein C was prepared from a crude protein C fraction obtained from commercially available prothrombin complex concentrate. The purification process was carried out using monoclonal antibody affinity chromatography. Monoclonal anti-protein C antibodies were produced in the following manner:

BALB/C mice were immunized with 100 μg human protein C by intraperitoneal injection at two-week intervals. After six weeks, another 50 μg of human protein C were injected and fusion was carried out three days later. The myeloma cell line (P3-X-63-AG8-653, $1.5\times10^7$ cells) was mixed with $1.7\times10^8$ mouse spleen cells and fused according to the modified method of Köhler & Milstein by using PG 1500 (Köhler G., Milstein C., Nature 256 (1975), 495–497).

Positive clones, assayed by means of ELISA, were subcloned twice. Ascites production was effected by injection of $5\times10^6$ hybridoma cells per BALB/C mouse two weeks after Pristan treatment.

The immunoglobulin was purified from ascites by means of ammonia sulfate precipitation, subsequent chromatography on QAE-Sephadex and final chromatography on Sephadex G200. To reduce the risk of transmission of murine viruses, the antibody was subjected to a further virus inactivation step prior to immobilization, e.g., as disclosed in EP-B-0 159 311 or EP-A-0 519 901. The monoclonal antibodies thus obtained were coupled to CNBr-Sepharose 4B (Pharmacia). The following buffers were used for the purification of protein C by means of affinity chromatography:

Absorption buffer: 20 mmol Tris, 2 mmol EDTA, 0.25 mmol NaCl and 5 mmol benzamidine; Washing buffer: 20 mmol Tris, 1 mol NaCl, 2 mmol benzamidine, 2 mmol EDTA, pH 7.4; Elution buffer: 3 mol NaSCN, 20 mmol Tris, 1 mol NaCl, 0.5 mmol benzamidine, 2 mmol EDTA.

EXAMPLE 2

Affinity Chromatography Purification

The prothrombin complex concentrate was dissolved in the absorption buffer of Example 1, with about 10 g of the prothrombin complex concentrate being employed for a 20 ml monoclonal antibody column. Subsequently, the dissolved prothrombin complex concentrate was filtered, centrifuged at 20,000 r.p.m. for 15 min. and sterilely filtered through a 0.8 μm filter. The sterilely filtered and dissolved prothrombin complex concentrate was applied to the column at a flow rate of 10 ml/h. Subsequently, the column was washed free of protein with the washing buffer of Example 1, the bound protein C was eluted by means of the elution buffer of Example 1 at a flow rate of 5 ml/h and the fractions containing eluted protein C were collected and pooled. The eluted protein C was dialyzed against a buffer (0.2 mol/l Tris, 0.15 mol glycine and 1 mmol EDTA, pH 8.3). Protein C antigen concentration was determined using the method described by Laurell, and protein C activity was determined using Protac activation.

The protein C eluate thus obtained was then finished to a pharmaceutically applicable preparation in the following manner:

The eluate was first subjected to ultrafiltration and diafiltration steps. Diafiltration was carried out with a buffer containing 150 mmol NaCl and 15 mmol trisodium citrate·2H$_2$O per liter, at a pH of 7.4. The filtrate was then freeze-dried and virus inactivated by a one-hour vapor treatment at 80°±5° C. and at 1375±35 mbar.

The lyophilized, virus inactivated material was then dissolved in a sterile isotonic NaCl solution and any antibodies or serum amyloid P potentially present in the preparation were eliminated by means of ion exchange chromatography on a Q-Sepharose column. The purified solution was concentrated by means of an additional ultrafiltration and diafiltration step. After this step, 10 g albumin, 150 mmol NaCl and 15 mmol trisodium citrate per liter were added to the solution obtained. The pH of the solution was 7.5. Neither murine immunoglobulin nor Factors II, VII, IX and X could be detected. Subsequently, the solution was sterilely filtered, filled in containers and lyophilized. The specific activity was 14 units protein C per mg. One unit of protein C activity is defined by the protein C activity in 1 ml normal plasma and is calibrated against the first international standard of protein C. An aminolytic assay was used as the activity test after activation of protein C by means of the snake venom Protac (purchased from Pentapharm).

EXAMPLE 3

Preparation of Activated Protein C

Activation of the purified protein C was effected by coupling 70 ml thrombin (500 NIH units/ml corresponding to approximately 2000 NIH units/mg protein) to CNBr-Sepharose 4B (Pharmacia), whereupon protein C was mixed with the thrombin gel at a ratio of about 6 units protein C to 1 unit thrombin at 37° C. and allowed to react for 3 hours under continuous shaking. The protein C activity was then determined by means of chromogenic substrate (S 2366). The activated protein C subsequently was sterilely filtered and finished to a pharmaceutical preparation by filling into containers and lyophilization.

EXAMPLE 4

Anti-nociceptive Effect

The anti-nociceptive action was demonstrated using the inflamed rat paw model by determining the pain threshold induced by local carrageenan administration into the rat paw with and without the administration of protein C.

Inflammation induced by local carrageenan administration (i.pl.) has been shown to increase bradykinin sensitivity of rat cutaneous nociceptors. See, Kirchhoff et al., Neuroscience Lett. 111:206–210 (1990). Subcutaneous administration of carrageenan into the rat paw produces an inflammatory edema characterized by infiltration of neutrophils, plasma extravasation, release and synthesis of histamine, bradykinins and prostaglandin $E_2$. Id. As such, the rat paw is a recognized model of the inflammatory process and may be utilized for studying the nociceptive effects attendant thereto. Id. Thus, the rat paw provides a recognized model for evaluating the anti-nociceptive effects of protein C and/or the activation peptide of protein C according to the present invention.

The pain threshold was measured in a manner analogous to the method described by Randall and Selitto (Randall LO and Selitto JJ: A method for measurement of analgesic activity on inflamed tissue, Arch. Int. Pharmacodyn. 111, 409–419, 1957). To this end, a mercury manometer was connected to a 10 ml syringe whose plunger was equipped with a short bullet-shaped peg. Increasing pressure was applied to the rat's paw through this syringe (20 mmHg/s).

The pain threshold was defined as the pressure in mmHg required to induce a flight (struggle) reaction.

Female Sprague-Dawley rats weighing between 250 and 350 g were used. Inflammation was produced by the intraplanter (i.pl.) injection of 3 mg carrageenan (Sigma Chemical Co., Cat. No., C-1013) suspended in 100 µl isotonic saline solution (0.9%) into the rat's paw.

The pain threshold was measured before (control value) and every hour up to six hours after the injection of carrageenan. The pain threshold measured after carrageenan injection was expressed in percent of the control value.

Unless otherwise specified, protein C was intravenously injected into a vein of the tail immediately upon the carrageenan injection. The injection volume was 2 ml/kg.

The results are schematically represented in FIG. 1. The pain threshold (expressed in percent of the control value) is shown on the ordinate and the dose of protein C (in units per kg) is shown on a logarithmic scale on the abscissa. Lines (a) and (b) correspond to the pain thresholds that have been measured without and with the influence of carrageenan, respectively. Curve (c) shows that the pain threshold, which was reduced under the influence of carrageenan, is raised by the administration of protein C (anti-nociceptive effect). From curve (c), which covers the dose range from 8 U/kg (10 animals), 25 U/kg (15 animals), 80 U/kg (20 animals), 250 U/kg (20 animals) to 800 U/kg, it can be seen that protein C has a significant, dose-dependent anti-nociceptive effect ($p<0.01$ for 80 units/kg; $p<0,001$ for 250 and 800 units/kg).

This anti-nociceptive effect of protein C is also detectable with subcutaneous administration. Furthermore, it could be demonstrated that a preparation containing activated protein C and the activation peptide of protein C also exhibits a dose-dependent anti-nociceptive effect.

EXAMPLE 5

In addition, it was demonstrated that intravenous administration of the non-selective β-adrenoceptor blocking drug propranolol antagonizes the anti-nociceptor effect of protein C. The protein C antagonizing effect of propranolol was observed within a dosage range of 0.03 to 1 mg/kg i.v. (cf. Table 1).

TABLE 1

Effect of propranolol on protein C-induced anti-nociception

|  | Pain threshold* | n |
|---|---|---|
| Carrageenan alone | 21 ± 3% | 15 |
| Carregeenan + protein C (800 U/kg) | 60 ± 6% | 15 |
| Carrageenan + protein C + propranolol (1 mg/kg) | 28 ± 5% | 10 |

*(Results are expressed in % of the pain threshold, measured 3 hrs after carrageenan administration in the rat paw model as described above.)

This antagonism is not limited to propranolol, however. As shown in Table 2 for pindolol, other β-blocking agents antagonize the effect of protein C in a dose-dependent manner as well.

TABLE 2

Effect of pindolol on protein C-induced anti-nociception

|  | Pain threshold* | n |
|---|---|---|
| Carrageenan alone | 22 ± 1.3% | 10 |
| Carrageenan + protein C (800 U/kg) | 65 ± 2.0% | 10 |
| Carrageenan + protein C + pindolol (0.3 mg/kg) | 24 ± 2.0% | 5 |

*(Results are expressed in % of the pain threshold, measured 3 hrs after carrageenan administration in the rat paw model as described above.)

After elimination of the sympathetic nervous tone by means of chemical sympathectomy with reserpine (7.5 mg/kg i.p., 18 to 24 hrs) and alpha-methyl-p-tyrosine (250 mg/kg i.p., 5 hrs), protein C still acts as a highly effective anti-nociceptive. But even in these sympathectomized animals, pindolol completely antagonizes the effect of protein C (Table 3). Thus, participation of the presynaptic sympathetic nervous system in the action of protein C may be excluded. Consequently, the action of protein C is due to a direct effect at postsynaptic β-adrenoceptors.

TABLE 3

Results in animals treated with resperine and alpha-methyl-p-tyrosine

|  | Pain threshold* | n |
|---|---|---|
| NaCl contr. | 61.0 ± 6.8% | 5 |
| Carrageenan alone | 34.0 ± 10.3% | 5 |
| Carrageenan + protein C (800 U/kg) | 106.7 ± 18.1% | 5 |
| Carrageenan + protein C + pindolol (1 mg/kg i.v.) | 33.3 ± 4.6% | 5 |

*(Results expressed in % of the pain threshold, measured 3 hrs after carrageenan in the rat paw model as described above.)

The effect of protein C may be mimicked by β-sympathomimetic agents. For example, fenoterol, injected i.v., either 5 mg/kg at the beginning of the assay or 3 mg/kg at the 3 hr time point, results in a marked anti-nociceptive effect. It can thus be concluded that the stimulation of postsynaptic β-adrenoceptors produces an anti-nociceptive effect.

The biochemical action of the putative β-sympathomimetic effects of protein C is believed to be caused by binding to adrenergic β-receptors and by the stimulation of the membrane-bound enzyme adenylcyclase, which catalyzes the intracellular formation of cAMP from ATP. cAMP activates protein phosphokinases, which, in turn, transform inactive enzymes into active ones by means of phosphorylation. In this manner, lipolysis and glycogenolysis, for instance, are augmented by β-sympathomimetic stimulation.

The physiologic effects of protein C, resulting from its β-sympathomimetic action are manifold. The increase in cAMP within thrombocytes leads to the inhibition of thrombocytic function and prevents thrombin from binding to the surfaces of thrombocytes. Thus, protein C may be employed in the prevention of the formation of thrombocyte dependent blood clots, in particular in the arterial vascular system, by binding to platelet β-adrenoceptors. The β-adrenoceptor-stimulating effect of protein C results in a positive inotropic effect on the heart and in a relaxing effect on the smooth muscles (e.g., on the bronchioles). Thus, due to its β-sympathomimetic effect on the vascular system, protein C may be used to treat peripheral vascular disease. Intracoronary administration of activated protein C in dogs has been shown to lead to an increase in coronary blood flow which is due to its vasodilating action. This vasodilating action of protein C may be useful in the treatment of hypertension. Anti-inflammatory properties may also be attributable to the β-sympathomimetic effect of protein C. The β-sympathomimetic action of protein c induces the inhibition of histamine release in the lungs. Due to the β-sympathomimetic effect of protein C, protein C may be used as a tocolytic agent.

EXAMPLE 6

Effect of Antibody HPC-4 on Anti-nociceptive Effects

A dose response curve for protein C administered i.v. and protein C (i.v.) immediately followed by a solution of 1 mg/kg antibody HPC-4 (i.v.) was determined. The experiments were carried out essentially as set forth in Example 4.

As discussed above and disclosed in U.S. Pat. No. 5,202,253, incorporated herein by reference, HPC-4 is a calcium dependent monoclonal antibody which specifically recognizes a dodecapeptide sequence found in the activation region of protein C: $NH_2$-Glu-Asp-Gln-Val-Asp-Pro-Arg-Leu-Ile-Asp-Gly-Lys-COOH (SEQ. ID. NO. 2). The antibody was deposited by its inventors with the American Type Culture Collection as accession No. HB-9892 on Nov. 2, 1988 and it is available from ATCC. This antibody binds to the activation peptide of protein C (SEQ. ID. NO. 1), does not bind to activated protein C and can prevent the activation of protein C by thrombin-thrombomodulin. In addition, an in vivo therapeutic use for HPC-4 has been disclosed in WO 94/02172, which provides that the antibody administered in vivo can block the activation of protein C. Domestic pigs treated with HPC-4, that subsequently underwent partialthickness skin graft harvesting to create a microvascular wound, underwent significantly less blood loss when compared to saline control animals.

Figure 2:
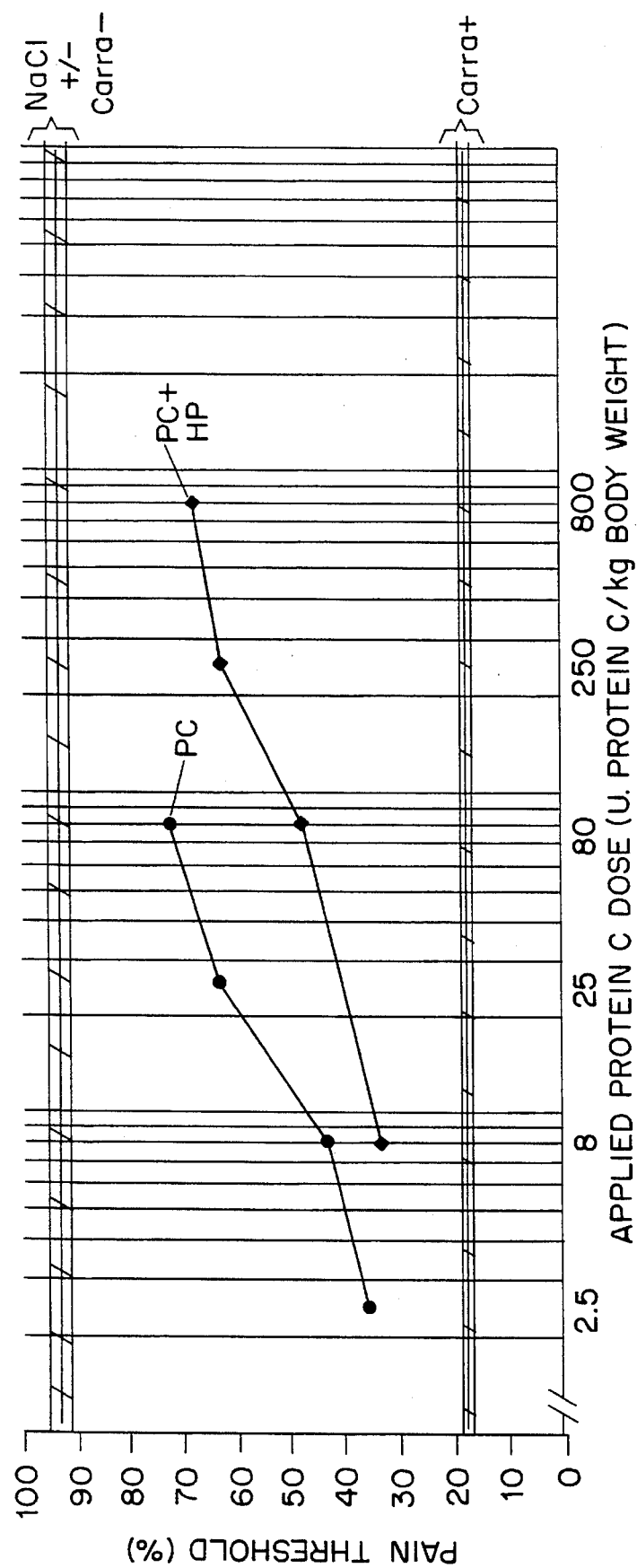
FIG. 2 is a graph depicting the anti-nociceptive effect in the rat paw model in a dose responsive manner to protein C and a reduced dose response in the presence of antibody HPC-4.

The results of the antagonistic effect of HPC-4 on the anti-nociceptive effect of protein C in experiments utilizing the rat paw model are shown in FIG. 2. The administered dose of protein C in I.U. per kg body weight is plotted on the X-axis. The Y-axis gives pain threshold in % (as above). The dose of protein C is given as a dot (·); the dose of protein C+HPC-4 is given as a rhombus (♦). Each point represents the average of five carrageenan-treated animals. Sodium chloride controls (no administered carrageenan) represent negative controls showing no pain, based on 13 animals ($\bar{X}\pm SX$).

As can be seen from FIG. 2, the dose response curve of protein c is shifted to the right by a factor of about 9 when HPC-4 is administered with the protein C. In pharmaceutical preparations containing activated protein C, HPC-4 prevents the anti-nociceptive effect only when free activation peptide (SEQ. ID. NO. 1) is added together with activated protein C.

The bars at the bottom of the graph (between 15–20% pain threshold) represent animals treated with carrageenan in the absence of protein C.

Thus, it is clear that the activation peptide of protein C has anti-nociceptive activity.

EXAMPLE 7

Preparation of the Activation Peptide of Protein C

The activation peptide of protein C having the amino acid sequence, $NH_2$-Asp-Thr-Glu-Asp-Gln-Glu-Asp-Gln-Val-Asp-Pro-Arg-COOH (SEQ. ID. NO. 1), was synthesized by solid phase synthesis according to the method of L. A. Carpino, *J. Org. Chem.* 37:3404 (1972), using the FMOC technique with 9-fluoren-methyloxycarbonyl (FMOC)-groups and activation with benzotriazol-1-yl-oxy-tris-pyrrolidino-phosphonium hexafluorophosphate (according to J. Martinez et al., *J. Med. Chem.* 28:1874 (1988), J. Coste et al., *Tetrahedron Letters* 31:205(1990) and C. E. Olsen et al., *Tetrahedron Letters* 32:7617 (1991)). The peptide chain was synthesized in a step by step fashion by means of a Milligen 9050 Pep-Synthesizer. Afterwards, the peptide was cleaved to remove the FMOC group and purified using reversed phase chromatography on Nukleosil 115 C18 (5 μ) and eluted with an acetonitrile/water gradient from 0 to 70% acetonitrile, in 30 minutes. The eluent contained 0.1% trifluoroacetic acid; the flow rate amounted to 1.5 ml per min. The fractions containing the activation peptide were pooled and dried.

The identity of the peptide was certified by the automated Edman decay on an Applied Biosystems 477A Protein Sequencer (P. Edman, *Acta Chem. Scand.* 4:283–293 (1950), P. Edman, *Acta Chem. Scand.* 7:700–701 (1953), P. Edman, *Acta Chem. Scand.* 10:761–768 (1956), P. Edman et al., *Eur. J. Biochem.* 1:80–91 (1967) and P. Edman et al., in Protein Sequence Determination (S. B. Needleman, ed., pp 232–279 (1975), Springer, Berlin, Heidelberg, N.Y.) Further characterization of the purity and identity of the peptide was done by $^{252}Cf$ plasma desorption mass spectrometry according to the method of D. F. Torgerson et al., *Biochem. Biophys. Res. Commun.* 60:616 (1974). The molecular mass of 1067.31 could be verified using this method.

EXAMPLE 8

Peptides having the amino acid sequence of β-endorphin ($NH_2$-Tyr-Gly-Gly-Phe-Met-Thr-Ser-Glu-Lys-Ser-Gln-Thr-Pro-Leu-Val-Thr-Leu-Phe-Lys-Asn-Ala-Ile-Ile-Lys-Asn-Ala-Tyr-Lys-Lys-Gly-Glu-COOH) (SEQ. ID. NO. 3), Met-enkephalin ($NH_2$-Tyr-Gly-Gly-Phe-Met-COOH) (SEQ. ID. NO. 4) and Leu-enkephalin ($NH_2$-Tyr-Gly-Gly-phe-Leu-COOH) (SEQ. ID. NO. 5) were synthesized, purified and characterized as described in Example 7. In addition, fusion peptides containing the amino acid sequence of the activation peptide of protein C, peptide bonded to β-endorphin, Met-enkephalin or Leu-enkephalin were also chemically synthesized as above.

EXAMPLE 9

Microencapsulation of Peptides

The peptides synthesized as described in Examples 7 and 8 were microencapsulated in liposomes by the following procedure:

A mixture of 50 mol % 1,2-di-palmitoyl-sn-glycero-3-phosphocholin, 20 mol % 1,2-di-palmitoyl-sn-glycero-3-phosphoglycerol, and 30 mol % cholesterol was dissolved in chloroform. The lipid concentration amounted to 10 mg/ml. The solvent was removed by means of rotary evaporation under reduced pressure at a temperature of 30° C. Following the complete removal of the solvent, the vacuum was held for 30 minutes at 30 mbar, and further 6 hours at 0.1 mbar. The resulting phospholipid film was hydratized at room temperature by addition of buffer (20 mM Tris, 150 mM NaCl, pH 7.4).

The phospholipid suspension thus obtained was combined with a peptide (e.g., SEQ. ID. NO. 1 or SEQ. ID. NO. 1 admixed with or fused to SEQ. ID. NOS. 3–5) to prepare a mixture containing 0.1 mg peptide and 1.0 mg lipid. The mixture was lyophilized. The lyophilate was again suspended in water in order to form a dispersion of multilamellar vesicles. This dispersion was extruded through two overlayed 100 nm polycarbonate filters by means of a 10 ml-Thermo Barrel Extruder, Lipex Biomembranes Inc., Vancouver, Canada. The extruded solution contained liposomes including peptide, and free peptide. Free peptide was removed by chromatography on Superose® 6 HR 10/30 (Pharmacia), using a buffer containing 20 mM Tris-HCl, 150 mM NaCl, pH 7.4. The fractions obtained in the void volume contained the peptide containing liposomes, and were pooled and lyophilized.

A microencapsulated peptide preparation for in vivo use was dispersed in 0.9% (w/v) NaCl solution.

Such a preparation contains about 1–1000 µg phospholipid and about 1–1000 µg peptide. Preferably microencapsulated peptide preparations for in vivo application contain about 10–1000 µg phospholipids together with about 1–100 µg peptide.

Thus, the ratio of peptide to lipid ranges from about 1:100 to 1:1 (w/w), with the preferred ratio being in the range of about 1:100 to 1:5 (w/w).

EXAMPLE 10

Anti-nociceptive Effect of the Activation Peptide of Protein C

The anti-nociceptive effects of the activation peptide of protein C (SEQ. ID. NO. 1) prepared as described in Example 7 were determined essentially as described in Examples 4 and 6. In the test animals, the peptide was administered i.v. to rats in a concentration of between 3.125 µg/kg and 50 µg/kg, each, in a constant injection volume of 2 ml/kg, simultaneously with intraplantar (i.pl.) administration of carrageenan into the rat's paw to induce an inflammatory response and pain. In a second set of test animals, antibody HPC-4 (1 mg/kg) was administered i.v. immediately following i.v. administration of the peptide (SEQ. ID. NO. 1). The anti-nociceptive effects of the peptide (SEQ. ID. NO. 1) administration and antagonism thereof by antibody HPC-4 as measured 6 hours later are shown in FIG. 3.

Figure 3:
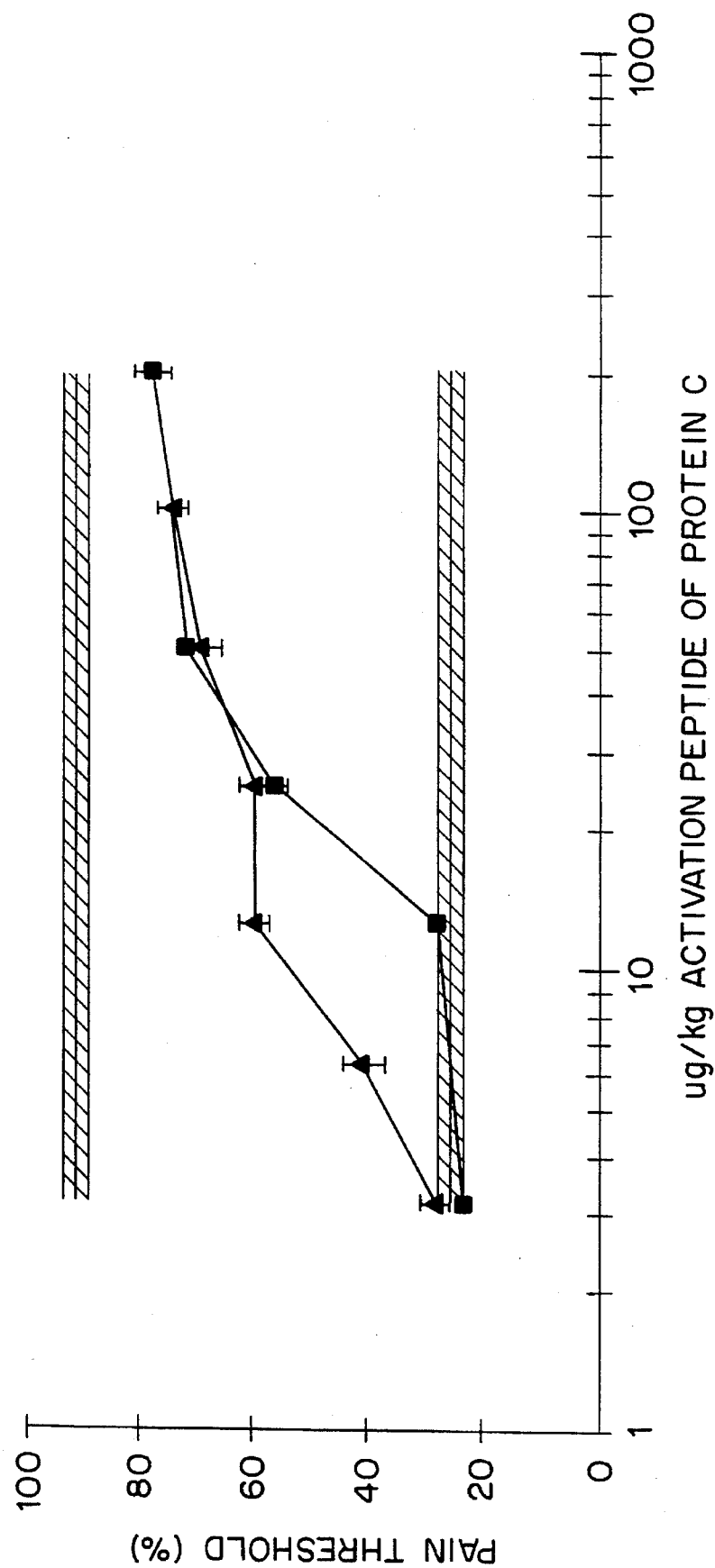
FIG. 3 is a graph depicting the anti-nociceptive effect in the rat paw model in a dose responsive fashion to the activation peptide of protein C and a reduced dose response in the presence of antibody HPC-4.

In FIG. 3, the animals receiving only the peptide (SEQ. ID. NO. 1) are represented by (▲) and those receiving the peptide (SEQ. ID. NO. 1) and HPC-4 are represented by (■). The X-axis provides the amount of the peptide (SEQ. ID. NO. 1) administered in µg/kg. The Y-axis provides the pain threshold in %.

Each point is represented with standard errors. The test groups were as follows:

(1) Three (3) mg/100 µl carrageenan were administered i.pl. six hours before administering the following amounts of the peptide (SEQ. ID. NO. 1) i.v.:
3.125 µg, 6.25 µg, 12.5 µg, 25 µg and 50 µg/kg (10 animals each); 100 µg/kg (5 animals)
The results are plotted as solid triangles (♦) ±S.E.

(2) Three (3) mg/100 µl carrageenan was administered i.pl. simultaneously with the following amounts of the peptide, followed by i.v. administration of 1 mg/kg antibody HPC-4:
3.125 µg, 12.5 µg, 25 µg, 50 µg, 200 µg/kg
The results are plotted as solid squares (■) ±S.E.
Control groups were as follows:

(3) Lower bar: 3 mg/100 µl carrageenan (i.pl.) (25 animals)

(4) Upper bar: 100 µl 0.9% NaCl (i.pl.) (25 animals)

It is clear from the above that the activation peptide of protein C (SEQ. ID. NO. 1) has an anti-nociceptive effect, which is antagonized by antibody HPC-4.

EXAMPLE 11

Effects of Protein C on Vascular Permeability

Examples 4 and 5 show that the pain threshold of the rat was raised when protein C was administered to the animal intravenously, indicating that the animals became less susceptible to pain induced by intraplantar injection of carrageenan. Moreover, when protein C was administered to the animals, signs of inflammation, such as oedema, were reduced.

In addition, Example 5 showed that the anti-nociceptive and anti-inflammatory effects of protein C are nearly eliminated by antagonists, such as pindolol or propanolol, which are both β-adrenoceptor blocking drugs. On the other hand, the effects of protein C were mimicked by the β-sympathomimetic agent Fenoterol. Thus, protein C appears to mediate stimulation of β-adrenoceptors in vivo, indicating another use as an anti-hypertensive therapy by inducing peripheral vasal dilatation or therapy of asthma by dilatation of smooth muscles of the bronchi. In addition protein C may be useful in inducing positive inotropic and chronotropic effects on the heart.

In the rat paw studies, the results of histological examination of the rat paws following administration of protein C to the rat showed a reduced number of perivascular leukocytes compared to the untreated animals was found. Thus, protein C appears to have an effect on vessel permeability, which allows the migration of leukocytes through the blood vessel into the perivascular region.

The effect of protein C on capillary leakage in guinea pigs was studied in order to confirm the efficacy of protein C in antagonizing enhanced vessel permeability in anesthetized guinea pigs. The study was carried out as follows:

After intravenous administration of Evan's Blue, anesthetized guinea pigs received either a protein C concentrate or a formulation buffer. Thereafter, the test animals were treated with histamine or thrombin intracutaneously to induce enhanced vessel permeability, or with saline as a control. The animals were then examined visually for the occurrence of discoloration of the resulting wheals. The results are depicted in FIG. 4 (histamine treatment, protein C or saline), FIG. 5 (thrombin treatment, protein C or saline) and FIG. 6 (thrombin treatment, buffer or saline).

In these studies, a colorless wheal was recorded as a negative observation (i.e., no disturbance in permeability), whereas a blue skin coloration at the injection site was defined as a positive observation (i.e. increased vessel permeability). The percentage of positive wheals among total wheals produced by the same substance and does within each group of treated animals (n=12 per treatment group) was calculated.

Figure 4:
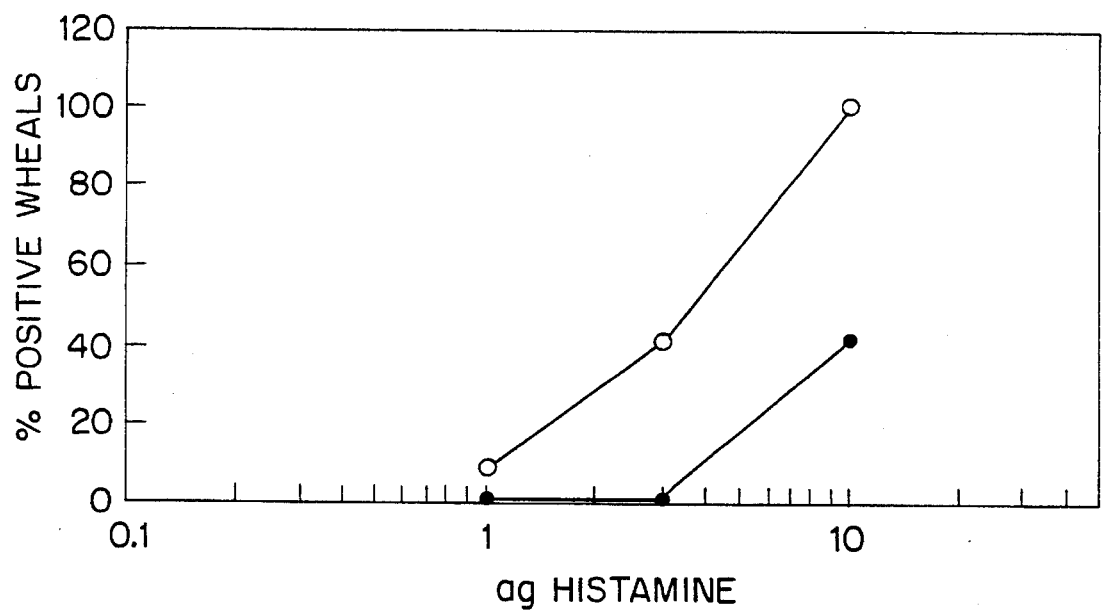
FIG. 4 is a graph depicting the effect of protein C on histamine-induced enhanced vascular permeability in guinea pigs.

The results in FIG. 4 plot the percent (%) positive (blue colored) wheals after intracutaneous injection of varying amounts of histamine (shown on the Y-axis). o and ● represent the effects of i.v. administered saline (n=12) and i.v administration of 800 IU protein C/Kg body weight (n=12), respectively.

Figure 5:
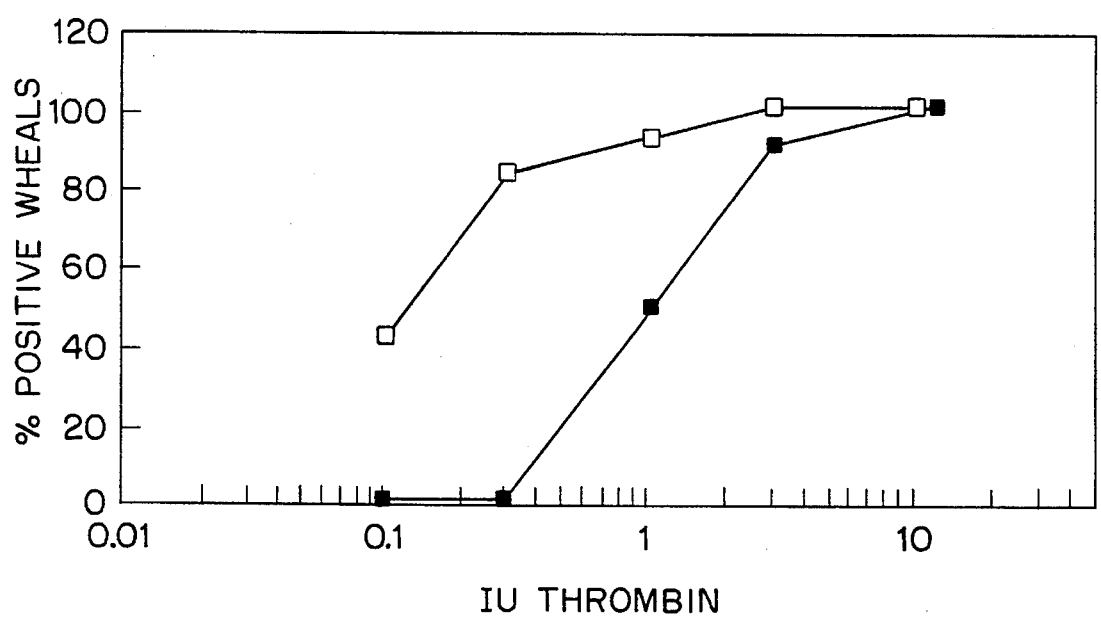
FIG. 5 is a graph depicting the effect of protein C on thrombin-induced enhanced vascular permeability in guinea pigs.

The results in FIG. 5 plot the percent (%) positive wheals after intracutaneous injection of varying amounts of thrombin (shown on the X-axis). □ and ■ represent the effects of i.v. administered saline (n=12) and i.v administration of 800 IU protein C/Kg body weight (n=12), respectively.

Figure 6:
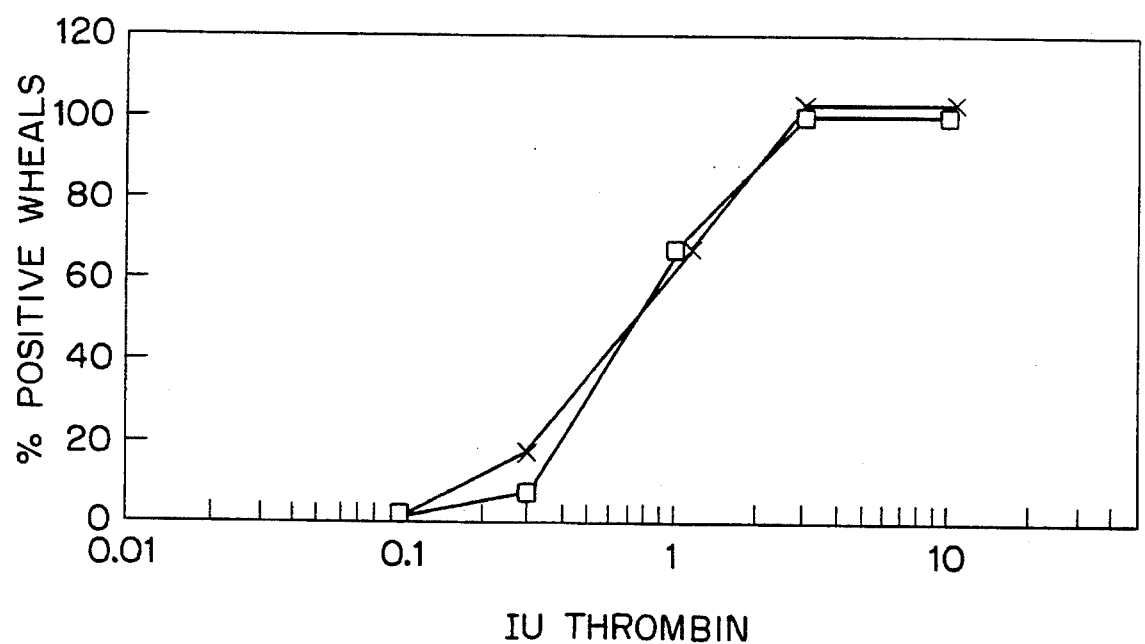
FIG. 6 is a graph depicting the effects of formulation buffer on thrombin-induced enhanced vascular permeability in guinea pigs.

The results in FIG. 6 plot the percent (%) positive wheals after intracutaneous injection of varying amounts of thrombin (shown on the X-axis). □ and X represent i.v. saline (n=12) and i.v. buffer (n=12) respectively.

The results show that pretreatment with protein C was effective in preventing the effects of both histamine and thrombin on increased endothelial permeability. There was a shift of the respective dose-response curves to the right by factors of 4 in the case of histamine (FIG. 4) and of 9 in the case of thrombin (FIG. 5). The formulation buffer, given in a volume and concentration analogous to the dose of protein C, had no effect on the dose-response curve of thrombin (FIG. 6).

---

We claim:

1. A method of treating and preventing pain resulting from inflammation comprising administering to a patient having or susceptible to pain occurring as a result of an inflammatory reaction an effective amount of an anti-nociceptive agent selected from the group consisting of protein C, activation peptide of protein C and mixtures thereof to treat or prevent the pain.

2. A method of treating and preventing inflammation comprising administering to a patient having or susceptible to an inflammatory process, a therapeutically effective amount of an anti-inflammatory agent selected from the group consisting of protein C, activation peptide of protein C and mixtures thereof to prevent or treat the inflammatory process.

3. A method according to claim 1 wherein the activation peptide comprises SEQ. ID. NO. 1.

4. A method according to claim 2 wherein the activation peptide comprises SEQ. ID. NO. 1.

* * * * *